United States Patent
Carroll et al.

(10) Patent No.: US 7,999,104 B2
(45) Date of Patent: Aug. 16, 2011

(54) METHODS FOR ONE-POT N-DEMETHYLATION/N-ACYLATION OF MORPHINE AND TROPANE ALKALOIDS

(75) Inventors: Robert James Carroll, St. Catharines (CA); Hannes Leisch, St. Catharines (CA); Tomas Hudlicky, St. Catharines (CA); D. Phillip Cox, Audubon, PA (US)

(73) Assignee: Brock University, St. Catharines, Ontario (CA)

( * ) Notice: Subject to any disclaimer, the term of this patent is extended or adjusted under 35 U.S.C. 154(b) by 1007 days.

(21) Appl. No.: 11/771,191

(22) Filed: Jun. 29, 2007

(65) Prior Publication Data

US 2009/0005565 A1 Jan. 1, 2009

(51) Int. Cl.
*C07D 489/02* (2006.01)
*C07D 489/00* (2006.01)
(52) U.S. Cl. .......................................... 546/45; 546/44
(58) Field of Classification Search .................. 546/45, 546/44
See application file for complete search history.

(56) References Cited

U.S. PATENT DOCUMENTS

| | | | |
|---|---|---|---|
| 4,472,253 | A | 9/1984 | Schwartz |
| 4,613,668 | A | 9/1986 | Rice |
| 6,399,078 | B1 | 6/2002 | Devico et al. |
| 6,440,688 | B1 | 8/2002 | Bruce |

FOREIGN PATENT DOCUMENTS

| | | |
|---|---|---|
| WO | 98/05667 | 2/1998 |
| WO | 01/34608 | 5/2001 |
| WO | 2005/047291 | 5/2005 |
| WO | 2005/113557 | 12/2005 |
| WO | 2006/104656 | 10/2006 |

OTHER PUBLICATIONS

Iijima, I. et al.: Studies in the (+) Morphinan series I. An alternate conversion of (+)-dihydrocodeinone into (+)-codeine. Heterocycles, vol. 6, pp. 1157-1165, 1977.*
Ripper, J.A. et al.: Photochemical N-demethylation of alkaloids. Bioorg. & Mrd. Chem. Lett., vol. 11, pp. 443-445, 2001.*

* cited by examiner

*Primary Examiner* — Charanjit Aulakh
(74) *Attorney, Agent, or Firm* — Occhiuti Rohlicek & Tsao LLP (57) ABSTRACT

The present invention provides a method for the N-demethylation and/or N-acylation of an N-methylated heterocycle such as morphine alkaloids or tropane alkaloids. The method comprises reacting the heterocycle with an acylating agent in the presence of a metal catalyst.

38 Claims, 1 Drawing Sheet

FIGURE 1

METHODS FOR ONE-POT N-DEMETHYLATION/N-ACYLATION OF MORPHINE AND TROPANE ALKALOIDS

FIELD OF THE INVENTION

The present invention relates to N-methylated compounds and methods for N-demethylation of same. In particular the present invention relates to morphine and tropane alkaloids and their derivatives and one-pot methods for N-demethylation and N-acylation of same.

BACKGROUND OF THE INVENTION

The semisynthesis of morphine-derived antagonists, such as naloxone, see compound 5 below, and naltrexone see compound 6 below, and other medicinally significant compounds, from opium-derived natural products traditionally involves standard procedures for demethylation followed by subsequent procedures such as oxidative procedures for the introduction of a C-14 hydroxyl group.

Most commercial procedures for the production of C-14 hydroxylated species take advantage of $\Delta_{7\text{-}8}$ unsaturated species, however compounds containing $\alpha,\beta$-unsaturated ketones have recently been identified as potential genotoxins because of their Michael acceptor character, and therefore it is desirable to find new routes to the oxygenated derivatives to avoid these intermediates.

Therefore any method that avoids these standard procedures may hold immense commercial potential for the production of morphine-derived antagonists, such as naloxone 5, naltrexone 6, and other medicinally significant compounds.

The development of a mild catalytic protocol for N-demethylation and acylation of ring-C saturated morphinans would simplify strategies toward C-14 oxygenated derivatives via potential use of an intramolecular process by tethered functionalisation anchored at the nitrogen atom.

Current methods for N-demethylation and/or N-acylation of morphine alkaloids are time consuming, expensive and hazardous. Thus there was an unmet need for improved methods. Furthermore, there is an increasing demand that production methods be environmentally friendly.

SUMMARY OF THE INVENTION

An investigation of the chemistry of morphine alkaloids and their derivatives, such as hydrocodone, 3, and oxycodone 4, led to the present invention which addresses the need for new methods for the production of morphine derivatives. The invention elucidates conditions for a one-pot oxidative N-demethylation and subsequent N-acylation of morphine alkaloids that is cost effective and safe.

The present invention provides a one-pot method for N-demethylation and subsequent acylation or carboxylation of N-methylated compounds, particularly morphine alkaloids and their derivatives or tropane alkaloids and their derivatives.

Preferred morphine compounds include thebaine, oripavine, 14-hydroxycodeinone, 14-hydroxymorphinone, morphine, codeine, hydromorphone, hydrocodone, oxymorphone, oxycodone, hydromorphol and oxymorphol.

Preferred tropane compounds are tropinone, tropane, tropine, atropine, cocaine or any other bicyclo-[3.2.1]-azabicyclic methylamines.

In a particularly preferred embodiment of this aspect the present invention there is provided a one-pot method for N-demethylation and subsequent acylation of hydrocodone.

In one aspect of the invention the method comprises reacting a heterocycle having the general structure:

with an acylating agent in the presence of a catalyst.

In one preferred embodiment, the acylating agent is an anhydride. Preferred anhydrides include acetic anhydride, iso-butyric anhydride, n-propanoic anhydride, decanoic anhydride, dodecanoic anhydride, cyclopropylcarbonyl anhydride, andydrides derived from carboxylic acids C1-C19 and mixed anhydrides derived therefrom.

In another preferred embodiment, the acylating agent is a dicarbonate. Preferred dicarbonates include carbonates derived from C1-C19 alcohols, dimethyl dicarbonate, di-tert-amyl dicarbonate, di-tert-butyl dicarbonate, diallyl pyrocarbonate, dibenzyl dicarbonate, diethyl pyrocarbonate, dimethyl dicarbonate, erythritol bis(carbonate) and mixed carbonates derived thereof.

In yet another aspect of the present invention there is provided a one-pot method for N-demethylation and subsequent carboxylation of morphine or tropane alkaloids and their derivatives to the corresponding carbonates. The acylating agent is preferably a dicarbamic anhydride such as N,N'-dimethylcarbamic anhydride, N,N'-diethylcarbamic anhydride, diphenylcarbamic acid anhydride, N,N'-diphenylcarbonic acid anhydride, N,N'-diphenyidicarbonic diamide, N,N'-(oxydicarbonyl)bisglycine dimethylester, pyrrole-1-carboxylic anhydride and mixtures thereof.

In a preferred embodiment of the invention, the catalyst is a metal catalyst selected from the group consisting of Pd(OAc)$_2$, PdCl$_2$, PdCl$_2$(PPh$_3$)$_4$, PdBr$_2$, Pd(acac)$_2$, Pd$_2$(dba)$_3$, Pd(dba)$_2$, Pd(PPh$_3$)$_4$, Cu, Fe, Ru, Co, Rh, Ir, Ni, Pd, Pt, Ge, Sn, Os, Cu, Ag, Au, Pb.

In one preferred embodiment, the method comprises the steps of treating the N-methylated compound with palladium, at least one anhydride but without any added solvent. In a preferred embodiment the palladium source is one of Pd(OAc)$_2$ or PdCl$_2$ and the anhydride is acetic anhydride. In a more preferred embodiment the palladium source is Pd(OAc)$_2$.

In another embodiment, the method comprises the steps of treating the N-methylated compound with a catalyst, at least one solvent and at least one dicarbonate. The solvent is typically benzene, dioxane, toluene or methanol. In a preferred embodiment the catalyst is Pd(OAc)$_2$, the solvent is dioxane and the dicarbonate is dimethyldicarbonate.

BRIEF DESCRIPTION OF THE DRAWINGS

These and other features of the invention will become more apparent from the following description in which reference is made to the appended drawings wherein.

DETAILED DESCRIPTION

As used herein, the term "acylation" and the related term "acylating agent" are used in the broadest sense to encompass any reaction in which an acyl group is added to a compound. This includes reactions in which the acyl group is derived from carboxylic acid. It also includes, for example, the addition of an acetyl group. Types of acylating agents that may be used in the present invention include, but are not limited to, anhydrides, dicarbonates, dicarbamic agents and other known acylating agents.

As used herein, the term "catalyst" is used broadly to refer to any metal, the salt thereof or any other derivative. Catalysts for use in the present invention include, but are not limited to Al, Ag, Au, Ge, Pb, Lr, Ni, Ru, Zn, Fe, Sn, Ru, Co, Rh, Ir, Ni, Pd, Pt, Ti, Os, Cu, Rh, Pd, Pd(OAc)$_2$, PdCl$_2$, PdBr$_2$, PdO, RhCl$_3$, PtO$_2$, RhCl(PPh$_3$)$_3$, Rh/Al, Pd/C, Pt/C, Pd on CaCO$_3$/Pb, Pd/Al, PtCl$_2$ and PtCl$_4$.

In particular the invention provides a method for catalysed N-demethylation and/or N-acylation wherein the N-methylated heterocycle is a morphine alkaloid or a derivative thereof or a tropane alkaloid or derivative thereof.

The morphine alkaloid derivatives are preferably selected from the group consisting of thebaine, oripavine, 14-hydroxycodeinone, 14-hydroxymorphinone, morphine, codeine, hydromorphone, hydrocodone, oxymorphone, oxycodone, hydromorphol and oxymorphol. In a preferred embodiment the morphine alkaloid derivative is hydrocodone.

Tropane derivatives are preferably selected from the group consisting of tropinone, tropane, tropine, atropine, cocaine, or any other bicyclo-[3.2.1]-azabicyclic methylamines.

An exemplary reaction in which hydrocodone is the N-methylated heterocycle is shown below:

X = C, CH, CH$_2$, CF$_2$, N, NR, O, S, SO, SO$_2$
Y = C, CH, CH$_2$, CF$_2$, N, NR, O, S, SO, SO$_2$
R, R$_1$, R$_2$, R', R'$_1$, R'$_2$ = H, SR, OR, SiRR$_1$R$_2$, NR$_1$R$_2$, Br, Cl, F, CF$_3$, C$_1$-C$_{19}$, CHO, COR, COOR, aryl, heterocycle
Z = O, N, S Various types of acylating agents can be used. The product that is obtained by the reaction can be customized through the selection of the starting material and the acylating agent.

One type of acylating agent that has been shown to be useful in the present invention is an anhydride.

A method according to claim 1 wherein the acylating agent is an anhydride in which Y is C, Z is O and X is C and whereby the acylating agent has the general structure:

Preferred anhydrides for use in the invention include acetic anhydride, iso-butyric anhydride, n-propanoic anhydride, decanoic anhydride, dodecanoic anhydride, cyclopropylcarbonyl anhydride, cyclobutylcarbonyl anhydride, anhydrides derived from carboxylic acids C1-C19 and mixed anhydrides derived therefrom.

Dicarbonates are also useful acylating agents for use in the present invention.

Examples of preferred dicarbonates include a mixed carbonate derivative of C1-C19 alcohols, dimethyl dicarbonate, di-tert-amyl dicarbonate, di-tert-butyl dicarbonate, diallyl pyrocarbonate, dibenzyl dicarbonate, diethyl pyrocarbonate, dimethyl dicarbonate, erythritol bis(carbonate) and mixed carbonates.

anhydride, N,N'diphenyldicarbonic diamide, N,N'(oxydicarbonyl)bisglycine dimethylester, pyrrole-1-carboxylic anhydride and mixtures thereof.

Catalysts that are useful in the invention are metal catalysts including elemental metals and salts thereof. Some examples are Cu, Fe, Ru, Co, Rh, Ir, Ni, Pt, Ge, Sn, Os, Cu, Ag, Au, Pb, Pd, $Pd(OAc)_2$, $PdCl_2$, $PdCl_2(PPh_3)_4$, $PdBr_2$, $Pd(acac)_2$, $Pd_2(dba)_3$, $Pd(dba)_2$, $Pd(PPh_3)_4$.

A preferred catalyst for use in the invention is a Pd catalyst, such as Pd, $PdCl_2$, $Pd(OAc)_2$, $Pd(PPh_3)_4$ and $Pd(dba)_2$. In a preferred embodiment the palladium catalyst is $Pd(OAc)_2$.

The amount of catalytic palladium is preferably in the range of about 0.01 equivalents to 1.2 equivalents. Preferably the amount of catalytic palladium is in the range of about 0.2 equivalents to 0.5 equivalents. More preferably the amount of catalytic palladium is about 0.2 equivalents.

The methods/reactions of the invention may optionally include the addition of a solvent such as water, benzene, dioxane, toluene, acetonitrile and C1-C4 alcohols or a mixture of any of these. In a preferred embodiment the solvent is dioxane. The amount of solvent added is usually in the range of about 0.1-100 mL/gram of alkaloid.

Figure 1:
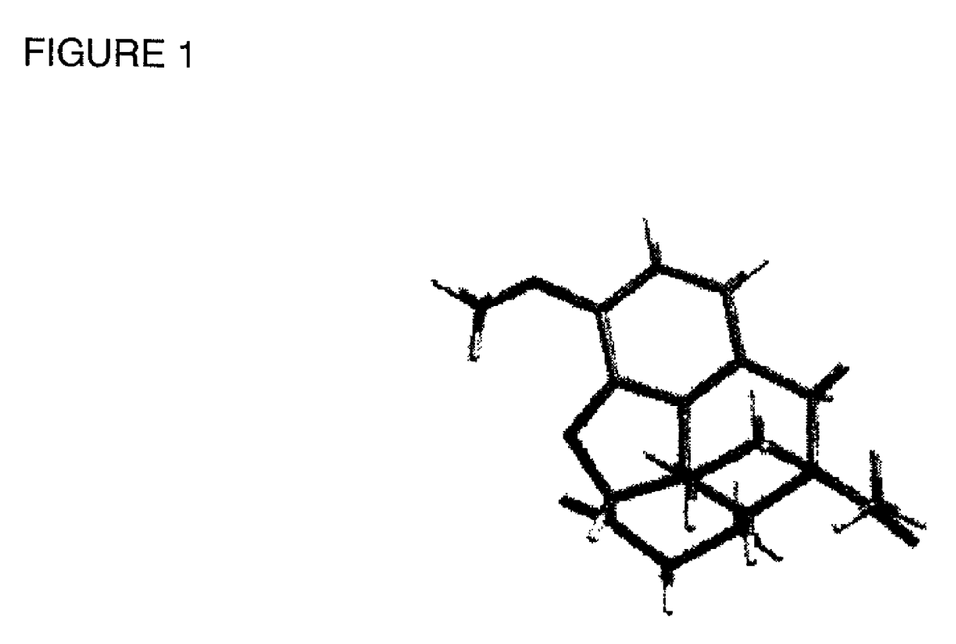
FIG. 1 shows an X-ray structure for N-acetylhydrocodone.

In one exemplary aspect of the invention, hydrocodone, identified in Scheme 1 below as 3, was treated with catalytic $Pd(OAc)_2$ in the presence of $Ac_2O$, and N-acetyl norhydrocodone 7 was isolated. The X-ray crystal structure of this novel morphine analogue is represented in FIG. 1.

SCHEME I

Alternatively, the acylating agent may be a dicarbamic anhydride in which Y is N, Z is O and X is N and the acylating agent has the general structure:

Preferred dicarbamic anhydrides include N,N'-dimethylcarbamic anhydride, N,N'diethylcarbamic anhydride, diphenylcarbamic acid anhydride, N,N'diphenylcarbonic acid

In another exemplary aspect of the invention, hydrocodone, identified in Scheme I above as 3, was treated with catalytic $Pd(OAc)_2$ in the presence of dimethyldicarbonate. This resulted in the production of N-methoxycarbonyl norhydrocodone 8.

The initial experiments using stoichiometric amounts of palladium demonstrated that benzene was an effective solvent. Further studies indicated that dioxane was a preferred solvent. Successive reduction of the catalyst loading to about 0.2 equivalents gave excellent results.

An interesting observation common to all conditions (described in greater detail in Examples 1a-j below) was the isolation of two isomers (7a, 7b) in a ratio of 3:1 in favour of the natural series.

75%

25%

Based on the success of the N-demethylation-acylation procedure, the reactivity of a series of anhydrides was explored. This resulted in the isolation of a novel range of N-acylated hydrocodone derivatives as described further in Example 2.

The utility of the invention was further demonstrated using other N-methylated heterocycles including tropane and its derivatives. The compatibility of the method to a range of functional groups such as ketones and esters was also demonstrated as shown in Example 3 below.

The above disclosure generally describes the present invention. It is believed that one of ordinary skill in the art can, using the preceding description, make and use the compositions and practice the methods of the present invention. A more complete understanding can be obtained by reference to the following specific examples. These examples are described solely to illustrate preferred embodiments of the present invention and are not intended to limit the scope of the invention. Changes in form and substitution of equivalents are contemplated as circumstances may suggest or render expedient. Other generic configurations will be apparent to one skilled in the art. All journal articles and other documents such as patents or patent applications referred to herein are hereby incorporated by reference.

EXAMPLES

Although specific terms have been used in these examples, such terms are intended in a descriptive sense and not for purposes of limitation. Methods of chemistry referred to but not explicitly described in the disclosure and these examples are reported in the scientific literature and are well known to those skilled in the art. A list of references is appended and these references are hereby incorporated by reference.

Example 1

General Procedure for Demethylation/Acylation

Tertiary amine (0.1 mmol, 1.0 eq.) was dissolved in acetic anhydride (1 ml) and Pd(OAc)$_2$ (0.01 mmol, 0.1 eq.) added. The reaction was heated at 80° C. for 15 hours, cooled to room temperature and passed through a plug of silica using CHCl$_3$: MeOH:NH$_4$OH 80:20:1 as eluent. The volatiles were removed in-vacuo, and the residue suspended in NaHCO$_3$. The aqueous phase was extracted with CHCl$_3$, and the combined organic extracts washed with 1M HCl and brine before being dried over magnesium sulphate, filtered and the volatiles removed in-vacuo to yield the acyl product.

It will be understood by a person skilled in the art that the above description for Example 1 is provided for the general procedure. The examples shown below in Examples 1a-1j follow the general procedure outlined above, and shown in Scheme I from compound 3 to 7, but include the use of different sources of palladium and different amounts of Pd(OAc)$_2$, where applicable, and the use of different solvents, as indicated in the table below.

Examples 1a-j

N-Demethylation-Acetylation of Hydrocodone (3)

| Example | Conditions (15 hours unless otherwise noted) | Yield of (7) % |
|---|---|---|
| 1a | Pd(OAc)$_2$ (1.2 equiv), MeCN, Ac$_2$O, 80° C. | <5% |
| 1b | PdCl$_2$ (1.2 equiv), benzene, Ac$_2$O, 80° C. | 50% |
| 1c | Pd(OAc)$_2$ (0.2 equiv), benzene, Ac$_2$O, 80° C. | 67% |
| 1d | Pd(dba)$_2$ (0.5 equiv), benzene, Ac$_2$O, 80° C. | 76% |
| 1e | Pd(OAc)$_2$ (0.2 equiv), dioxane (dry), Ac$_2$O, 80° C. | 80% |
| 1f | Pd(OAc)$_2$ (0.2 equiv), dioxane (wet), Ac$_2$O, 80° C. | 80% |
| 1g | Pd(OAc)$_2$ (0.2 equiv), toluene, Ac$_2$O, 80° C. | 67% |
| 1h | Pd(OAc)$_2$ (0.2 equiv), MeOH, Ac$_2$O, rt, 3 days | 15% |
| 1i | PdCl$_2$ (0.2 equiv), dioxane, Ac$_2$O, 80° C. | 17.1% |
| 1j | Pd(PPh$_3$)$_4$ (0.2 equiv), dioxane, Ac$_2$O, 80° C. | 76% |
| 1k | Pd(dba)$_2$ (0.2 equiv), dioxane, Ac$_2$O, 80° C. | 72% |

N-Acetyl-N-norhydrocodone (7) was isolated as a mixture of two isomers in a ratio of 3:1 in 80% yield.

(Major isomer) R$_f$ 0.3 (96:4 DCM:MeOH); mp (CHCl$_3$/Hex) 99-100° C.; FTIR ($v_{max}$ cm$^-$) film: 2929, 1727, 1628, 1505, 1436, 1325, 1274, 1241, 1121, 1061, 1026 $^1$H NMR (CDCl$_3$, 600 MHz): 6.77 (d, J=8.2 Hz, 1H), 6.68 (d, J=8.2 Hz, 1H), 5.25-5.28 (m, 1H), 4.69 (s, 1H), 3.94 (s, 3H), 3.67 (dd, J=13.8, 4.8 Hz, 1H), 3.09 (dt, J=13.2, 4.0 Hz, 1H), 2.91 (dd, J=18.6, 6.1 Hz, 1H), 2.67 (d, J=18.5 Hz, 1H), 2.32-2.51 (m, 3H), 2.14 (s, 3H), 1.91-2.02 (m, 3H), 1.20-1.32 (m, 1H) ppm; $^{13}$C NMR (CDCl$_3$, 125 MHz): 206.8, 169.0, 145.6, 143.2, 126.0, 124.9, 120.4, 115.1, 91.0, 56.8, 47.6, 47.3, 41.2, 40.5, 39.9, 35.5, 28.4, 25.3, 22.1 ppm; MS (EI) m/z (%) 327 (24), 241 (23), 117 (10), 87 (68), 86 (21), 85 (72), 84 9 (31), 83 (100), 57 (12), 49 (13), 48 (12), 47 (28), 43 (23), 41 (10); HRMS calc. for C$_{19}$H$_{21}$NO$_4$: 327.1470, found 327.1483.

(Minor isomer) $^1$H NMR (CDCl$_3$, 600 MHz): 6.77 (d, J=8.2 Hz, 1H), 6.67 (d, J=8.2 Hz, 1H), 4.70 (s, 1H), 4.56 (dt, J=14.2, 3.1 Hz, 1H), 4.27-4.31 (m, 1H), 3.94 (s, 3H), 3.67 (dd, J=13.8, 4.8 Hz, 1H), 3.09 (dt, J=13.2, 4.0 Hz, 1H), 2.97 (dd, J=18.2, 5.8 Hz, 1H), 2.76 (d, J=18.1 Hz, 1H), 2.53-2.61 (m, 1H) 2.32-2.51 (m, 2H), 2.14 (s, 3H), 1.91-2.02 (m, 2H), 1.20-1.32 (m, 1H) ppm; $^{13}$C NMR (CDCl$_3$, 125 MHz): 206.7, 168.7, 145.6, 143.6, 126.0, 123.9, 120.3, 115.3, 91.0, 56.8, 53.8, 47.2, 42.1, 39.7, 35.4, 34.7, 29.2, 25.5, 21.9 ppm MS (EI) m/z (%) 327 (24), 241 (23), 117 (10), 87 (68), 86 (21), 85 (72), 84 (31), 83 (100), 57 (12), 49 (13), 48 (12), 47 (28), 43 (23), 41 (10) HRMS calc. for C$_{19}$H$_{21}$NO$_4$: 327.1470, found 327.1483.

Example 2

Reactivity of a Series of Anhydrides

The reactivity of a series of anhydrides was explored following the general procedure outlined in Example 1.

| Example | Anhydride | Time (hrs) | Yield (%) | Product |
|---|---|---|---|---|
| 2a | acetic anhydride | 15 | 80 | 7 |
| 2b | Cyclopropanecarboxylic anhydride | 24 | 76 | 9 |
| 2c | iso-butyric anhydride | 24 | 13 | 10 |
| 2d | n-propanoic anhydride | 24 | 53 | 11 |
| 2e | decanoic anhydride | 120 | 36 | 12 |
| 2f | Dodecanoic anhydride | 120 | 43 | 13 |

Scheme IV below shows the range of N-acylated norhydrocodone derivatives that resulted from each of Examples 2a-2f, outlined above.

SCHEME IV

R = $CH_3$ (7)
R = Cyclopropyl (9)
R = $CH(CH_3)_2$ (10)
R = $CH_2CH_3$ (11)
R = $(CH_2)_8CH_3$ (12)
R = $(CH_2)_{10}CH_3$ (13)

N-iso-butyryl-N-demethylhydrocodone (10) was isolated as a mixture of two isomers in a ratio of 13:4 in 13% yield.

(Major isomer) FTIR ($v_{max}$ cm$^{-1}$) film: 3444, 2970, 2933, 1728, 1643, 1634, 1505, 1435, 1327, 1276, 1260, 1177, 1156, 1032, 958, 754; $^1$H NMR (CDCl$_3$, 300 MHz): 6.77 (d, J=8.2 Hz, 1H), 6.68 (d, J=8.6 Hz, 1H), 5.26-5.33 (m, 1H), 4.68 (s, 1H), 3.94 (s, 3H), 3.74-3.84 (m, 1H), 2.73-3.12 (m, 3H), 2.62 (d, J=18.5 Hz, 1H), 2.28-2.51 (m, 3H), 1.87-2.06 (m, 3H), 1.20-1.30 (m, 1H), 1.19 (d, J=6.8 Hz, 3H), 1.12 (d, J=7.02 Hz, 3H); $^{13}$C NMR (CDCl$_3$, 75.5 MHz): 206.92, 175.35, 145.57, 143.18, 126.18, 125.08, 120.36, 115.13, 90.97, 56.78, 47.61, 47.39, 41.38, 39.92, 39.35, 35.86, 30.46, 28.45, 25.35, 19.62, 19.08; MS (EI) m/z (%): 355 (34.5), 242 (12.5), 241 (33.7), 115 (98.6), 100 (12.5), 88 (12.7), 87 (16.0), 86 (65.9), 84 (100.0), 72 (23.7), 55 (10.7), 49 (19.5), 47 (23.7), 43 (52.9), 41 (15.1); HRMS (EI) calcd for $C_{21}H_{25}NO_4$: 355.1784; found 355.1777.

Cyclopropylcarbonyl-demethyl-hydrocodone (9) was isolated as a mixture of two isomers in a ratio of 3:1 in 76% yield.
FTIR ($v_{max}$ cm$^{-1}$) film: 3448, 3007, 2929, 1728, 1631, 1505, 1438, 1327, 1275, 1115, 960, 753 (Major isomer) $^1$H NMR (CDCl$_3$, 600 MHz): 6.76 (d, J=8.2 Hz, 1H), 6.64-6.70 (m, 1H), 5.22-5.26 (m, 1H), 4.69 (s, 1H), 4.09 (dd, J=13.7, 4.6 Hz, 1H), 3.92 (s, 3H), 3.12 (dt, J=13.2, 3.7 Hz, 1H), 2.89 (dd, J=18.3, 6.2 Hz, 1H), 2.65 (d, J=18.5 Hz, 1H), 2.31-2.63 (m, 5H), 2.04 (dt, J=12.5, 5.1 Hz, 1H), 1.89-2.00 (m, 1H), 1.70-1.78 (m, 1H), 1.18-1.36 (m, 1H), 0.96-1.09 (m, 1H), 0.74-0.92 (m, 2H) $^{13}$C NMR (CDCl$_3$, 150 MHz): 207.1, 172.0, 145.6, 143.3, 126.2, 125.1, 120.4, 115.1, 91.1, 67.1, 56.7, 48.3, 47.4, 42.1, 39.9, 36.2, 29.7, 28.4, 11.5, 8.8, 7.6 (Minor isomer) $^1$H NMR (CDCl$_3$, 600 MHz): 6.76 (d, J=8.2 Hz, 1H), 6.64-6.70 (m, 1H), 4.73-4.77 (m, 1H), 4.70 (s, 1H), 4.50 (dd, J=13.9, 3.6 Hz, 1H), 3.92 (s, 3H), 2.99 (dd, J=18.0, 5.7 Hz, 1H), 2.80 (d, J=18.1 Hz, 1H), 2.31-2.63 (m, 5H), 2.04 (dt, J=12.5, 5.1 Hz, 1H), 1.89-2.00 (m, 1H), 1.81-1.83 (m, 1H), 1.57-1.65 (m, 1H), 1.18-1.36 (m, 1H), 0.96-1.09 (m, 1H), 0.74-0.92 (m, 2H) $^{13}$C NMR (CDCl$_3$, 150 MHz): 206.9, 171.9, 145.5, 143.1, 126.2, 125.1, 120.2, 114.9, 91.0, 67.1, 56.7, 48.3, 47.4, 41.2, 39.7, 35.7, 29.4, 25.3, 11.5, 7.5, 7.3 MS (EI) m/z (%): 354 (17), 353 (66), 301 (28), 300 (11), 242 (30), 241 (57), 240 (14), 213 (11), 199 (11), 185 (19), 164 (30), 141 (10), 129 (16), 128 (12), 127 (10), 115 (15), 114 (11), 113 (61), 112 (82), 111 (28), 109 (11), 99 (11), 98 (73), 97 (11), 88 (23), 87 (19), 86 (48), 85 (89), 84 (80), 83 (100), 82 (18), 72 (13), 71 (21), 70 (25), 69 (81), 68 (14), 60 (12), 59 (18), 58 (22), 57 (37), 56 (13), 55 (31), 49 (21), 48 (13), 47 (36), 45 (22), 44 (28), 43 (40), 42 (32), 41 (77) HRMS (EI) calcd for $C_{21}H_{23}NO_4$: 353.1627; found 353.1612.

N-n-propionyl-N-demethylhydrocodone (11) was isolated as a mixture of two isomers in a ratio of 3:1 in 53% yield.
(Major isomer) FTIR ($v_{max}$ cm$^{-1}$) film: 3436, 2918, 2849, 1727, 1634, 1505, 1437, 1276, 1118, 1031, 971 $^1$H NMR (CDCl$_3$, 600 MHz): 6.68 (d, J=8.2 Hz, 1H), 6.59 (d, J=8.3 Hz, 1H), 5.17-5.22 (m, 1H), 4.60 (s, 1H), 3.85 (s, 3H), 3.62 (dd, J=13.4, 5.0 Hz, 1H), 2.96 (dt, J=13.0, 3.8 Hz, 1H), 2.83 (dd, J=18.6, 6.0 Hz, 1H), 2.56 (d, J=8.5 Hz, 1H), 2.20-2.47 (m, 6H), 1.81-1.93 (m, 3H), 1.10 (t, J=7.7 Hz, 3H); $^{13}$C NMR (CDCl$_3$, 125 MHz): 206.9, 172.3, 145.6, 143.3, 126.2, 125.2, 120.5, 115.2, 91.1, 56.8, 47.9, 47.3, 41.4, 40.1, 39.5, 35.9, 28.5, 27.2, 25.4, 9.7; MS (EI) m/z (%): 341 (33.1), 242 (12.2), 241 (30.6), 188 (11.1), 185 (11.0), 167 (10.8), 149 (28.3), 129 (13.2), 113 (10.0), 102 (11.2), 101 (100.0), 72 (17.6), 71 (13.6), 70 (13.5), 57 (85.0), 56 (10.7), 55 (19.3), 43 (18.2), 41 (13.8) HRMS (EI) calcd for $C_{20}H_{23}NO_4$: 341.1627; found 341.1628.

N-n-decanoyl-N-demethylhydrocodone (12) was isolated as a mixture of two isomers in a ratio of 3:1 in 36% yield.
(Major isomer) FTIR ($v_{max}$ cm$^{-1}$) film: 3435, 2926, 2850, 1726, 1626, 1505, 1436, 1155, 1030, 892, 753 $^1$H NMR (CDCl$_3$, 600 MHz): 6.68 (d, J=8.2 Hz, 1H), 6.59 (d, J=8.0 Hz, 10 1H), 5.18-5.21 (m, 1H), 4.60 (s, 1H), 3.84 (s, 3H), 3.62 (dd, J=13.5, 4.6 Hz, 1H), 3.38 (m, 1H), 2.96 (dt, J=13.1, 3.8 Hz, 1H), 2.83 (dd, J=18.6, 6.1 Hz, 1H), 2.55 (d, J=18.4 Hz, 1H), 2.34-2.40 (m, 1H), 2.20-2.33 (m, 3H), 1.81-1.93 (m, 2H), 1.59-1.65 (m, 2H), 1.49-1.58 (m. 2H), 1.13-1.33 (m, 12), 0.81 (t, J=6.8 Hz, 3H); $^{13}$C NMR (CDCl$_3$, 125 MHz): 207.3, 171.9, 145.6, 143.4, 126.2, 124.9, 120.7, 115.1, 91.3, 56.7, 47.4, 41.3, 39.9, 39.7, 35.7, 34.0, 33.8, 31.9, 31.7, 29.5, 29.4, 28.4, 25.6, 25.4, 25.0, 22.7, 14.1; MS (EI) m/z (%): 439 (1.0), 224 (41.8), 172 (10.1), 143 (36.3), 100 (15.8), 99 (56.6), 98 (36.9), 83 (18.2), 82 (11.2), 70 (21.3), 67 (10.4), 61 (52.2), 57 (19.3), 56 (100.0), 55 (43.2), 44 (14.1), 43 (46.5), 41 (42.7); HRMS (EI) calcd for $C_{27}H_{37}NO_4$: 439.2723; found 439.2719.

N-n-dodecanoyl-N-demethylhydrocodone (13) was isolated as a mixture of two isomers in a ratio of 3.6:1 in 43% yield.

(Major isomer) FTIR ($v_{max}$ cm$^{-1}$) film: 3334, 2926, 2852, 1729, 1627, 1575, 1505, 1438, 1275, 1031, 965 $^1$H NMR (CDCl$_3$, 300 MHz): 6.77 (d, J=8.2 Hz, 1H), 6.67 (d, J=8.5 Hz, 1H), 5.24-5.32 (m, 1H), 4.69 (s, 1H), 3.93 (s, 3H), 3.66-3.76 (m, 1H), 3.42-3.58 (m, 1H), 2.98-3.11 (m, 1H), 2.91 (dd, J=18.6, 6.1 Hz, 1H), 2.63 (d, J=18.5 Hz, 1H), 2.23-2.52 (m, 3H), 1.87-2.04 (m, 4H), 1.54-1.79 (m, 4H), 1.20-1.47 (m, 15H), 1.01-1.20 (m, 3H), 0.89 (t, J=6.5 Hz, 3H); $^{13}$C NMR (CDCl$_3$, 75.5 MHz): 207.2, 171.8, 145.9, 143.3, 126.2, 125.2, 120.5, 115.2, 91.1, 56.8, 49.4, 47.6, 47.4, 41.4, 39.8, 35.9, 35.7, 34.2, 34.0, 32.1, 32.0, 29.7, 29.6, 29.5, 25.8, 25.4, 25.0, 22.8, 14.3; MS (El) m/z (%): 467 (2.5), 224 (21.4), 143 (17.6), 100 (10.0), 99 (27.0), 98 (17.4), 61 (23.2), 56 (100.0), 55 (19.9), 43(20.5), 41 (19.1); HRMS (El) calcd for C$_{29}$H$_{41}$NO$_4$: 467.3036; found 467.3037.

Example 3

N-Acylation of Tropane Alkaloids

The above procedure outlined in Example 3 was also applied to other N-methylated heterocyles, identified below in Examples 3a-3e.

Examples 3a-3e

| Example | Substrate | Conditions Pd(OAc)$_2$ 0.2 equiv. | Isolated yield % (conversion % by GCMS) |
|---|---|---|---|
| 3a | 14 | a) Ac$_2$O neat, 80° C., 14 hrs; b) PhH, Ac$_2$O, 80° C., 60 hrs; | a) 72% (100%); b) 48% (60%); 15 |
| 3b | 16 | Ac$_2$O neat, 80° C., 14 hrs | 70% (100%) 17 |
| 3c | 18 | Ac$_2$O neat, 80° C., 14 hrs | 19 43%; 20 35% |
| 3d | 21 | benzene, Ac$_2$O, 80° C., 14 hrs | 22 85% |

-continued

| Example | Substrate | Conditions Pd(OAc)$_2$ 0.2 equiv. | Isolated yield % (conversion % by GCMS) |
|---|---|---|---|
| 3e | 23 | 10 equiv. succinic anhydride, benzene, 80° C., 60 hrs, (1 equiv of Pd(OAc)$_2$ used) | 24<br>10% (50%) |

8-acetyl-8-aza-bicyclo[3.2.1]octan-3-yl 2-phenylacrylate (22)

R$_f$ 0.3 (96:4 DCM:MeOH); mp 104-107° C.; FTIR ($v_{max}$ cm$^{-1}$) film: 2953, 2922, 1714, 1635, 1495, 1445, 1424, 1327, 1196, 1167, 1076, 1034; $^1$H NMR (CDCl$_3$, 300 MHz): 7.29-7.42 (m, 5H), 6.37 (s, 1H), 5.89 (s, 1H), 5.25 (t, J=4.8 Hz, 1H), 4.59-4.68 (m, 1H), 4.04-4.13 (m, 1H), 2.22 (dt, J=15.3, 4.3 Hz, 1H), 2.05 (s, 3H), 1.78-2.15 (m, 7H) ppm; $^{13}$C NMR (CDCl$_3$, 75.5 MHz): 166.1, 165.8, 141.8, 136.7, 123.3, 128.2, 128.1, 127.0, 68.3, 54.2, 50.1, 37.3, 35.6, 28.6, 26.9, 21.5 ppm; MS (EI) m/z (%) 299 (18), 257 (16), 168 (15), 152 (28), 151 (32), 136 (18), 126 (10), 111 (14), 110 (100), 109 (38), 108 (17), 103 (38), 97 (10), 86(27), 84 (44), 83 (15), 82 (19), 81 (25), 80 (29), 77 (22), 71 (11), 69 (33), 68 (35) 67 (28), 57 (19), 55 (18), 47 (10), 43 (68), 41 (26); HRMS (EI) calcd for C$_{18}$H$_{21}$NO$_3$: 299.1521; found 299.1518; Anal. calcd for C$_{18}$H$_{21}$NO$_3$: C, 72.22%; H, 7.07%; found: C, 70.84%; H, 7.18%.

4-oxo-4-(3-oxo-8-aza-bicyclo[3.2.1]octan-8-yl)butanoic acid (24)

R$_f$ 0.3 (96:4:1 DCM:MeOH:AcOH); FTIR ($v_{max}$ cm$^{-1}$) film: 3416, 2959, 2924, 2852, 2645, 1715, 1618, 1459, 1413, 1199, 1178; $^1$H NMR (CDCl$_3$, 300 MHz): 4.95 (t, J=5.8 Hz, 1H), 4.52 (t, J=5.7 Hz, 1H), 2.65-2.94 (m, 6H), 2.43 (t, J=16.5 Hz, 2H), 2.00-2.29 (m, 2H), 1.65-1.92 (m, 2H) ppm; $^{13}$C NMR (CDCl$_3$, 75.5 MHz): 207.1, 176.7, 168.4, 53.7, 51.4, 49.4, 49.8, 29.9, 29.0, 28.3, 27.7 ppm.

Substitution of the Anhydride with Dimethyldicarbonate

Hydrocodone bitartrate (100 mg, 0.22 mmol, 1 eq.) was suspended in a mixture of benzene and dimethyldicarbonate; 1:1 (2 ml) and Pd(OAc)$_2$ was added. The reaction mixture was heated to 80° C. for 18 hrs, before it was cooled to rt and filtered through a plug of celite. The solvent was evaporated and the residue was taken up in CHCl$_3$ and the organic layer was washed with 1N HCl. The organic layer was dried over MgSO$_4$, the solvent was evaporated and the residue was purified by flash column chromatography (CHCl$_3$: MeOH; 100: 0→90:10) to give 25 mg of compound 8 as a mixture of 2 isomers in a ratio of 6:4 (33%) as colorless oil.

R$_f$ 0.55 (92:8; DCM: MeOH); FTIR ($v_{max}$ cm$^{-1}$) film: 3019, 2955, 2934, 2842, 2806, 1744, 1637, 1610, 1506, 1441, 1325, 1263, 1164, 1040; $^1$H NMR (CDCl$_3$, 600 MHz): 6.75 (d, J=8.2 Hz, 2H), 6.63-6.68 (m, 2H), 4.77-4.81 (m, 1H), 4.67-4.70 (m, 2H), 4.60-4.64 (m, 1H), 4.10 (dd, J=13.5, 5.0 Hz, 1H), 3.93-3.98 (m, 1H), 3.92 (s, 6H), 3.80-3.88 (m, 2H), 3.76 (s, 3H), 3.73 (s, 3H), 2.83-2.91 (m, 2H), 2.75-2.82 (m, 2H), 2.68-2.74 (m, 2H), 2.42-2.48 (m, 4H), 2.34-2.41 (m, 2H), 1.82-2.00 (m, 4H), 1.18-1.28 (m, 2H) ppm; $^{13}$C NMR (CDCl$_3$, 125 MHz): 207, 2, 155, 9, 155.5, 145.5, 143.1, 126.1, 124.9, 124.7, 120.4, 120.3, 114.9, 114.8, 91.2, 56.7, 52.9, 52.8, 50.9, 50.6, 47.24, 47.17, 41.5, 41.4, 40.7, 39.9, 39.8, 38.01, 37.97, 35.0, 34.8, 28.9, 28.5, 25.4, 25.3 ppm; HRMS (EI) calc. for C$_{19}$H$_{21}$NO$_5$: 343.1420, found: 343.1421.

All analytical data for compounds 9, 15, 17, 19, 20 are in agreement with that reported in the literature.

In addition to compounds 10, 11, 12 and 13, structures 22 and 24 are also novel compounds.

One or more currently preferred embodiments have been described by way of example. It will be apparent to persons skilled in the art that a number of variations and modifications can be made without departing from the scope of the invention as defined in the claims.

REFERENCES

1. Hageman, H. A. *Org. React.* 1953, 7, 198
2. Von Braun, J. *Chem. Ber.* 1900, 33, 1438
3. Yu, H.; Prisinzano, T.; Dersch, C. M.; Marcus, J.; Rothman, R. B.; Jacobsen, A. E.; Rice, K. C. *Bioorg. Med. Chem. Lett.* 2002, 12, 165.
4. Cooley, J. H.; Evain, E. J. *Synthesis* 1989, 1
5. Hobson, J. D.; McCluskey, J. G. *J. Chem. Soc.* 1967, 2015;
6. Montzka, T. A.; Matiskella, J. D.; Partyka, R. A. *Tetrahedron Lett.* 1974, 15, 1325
7. Rice, K. C. *J. Org. Chem.* 1975, 40, 1850
8. Olofson, R. A.; Schnur, R. C.; Bunes, L.; Pepe, J. P. *Tetrahedron Lett.* 1977, 1567
9. Kapnang, H.; Charles, G. *Tetrahedron Lett.* 1983, 24, 3233
10. Olofson, R. A.; Martz, J. T.; Senet, J.-P.; Piteau, M.; Malfroot, T. *J. Org. Chem.* 1984, 49, 2081
11. Greiner, E.; Spetea, M.; Krassnig, R.; Schüllner, F.; Aceto, M.; Harris, L. S.; Traynor, J. R.; Woods, J. H.; Coop, A.; Schmidhammer, H. *J. Med. Chem.* 2003, 46, 1758
12. Hamilton, G. L.; Backes, B. J. *Tetrahedron Lett.* 2006, 47, 2229
13. Ripper, J. A.; Tiekink, E. R. T.; Scammells, P. *J. Bioorg. Med. Chem. Lett.* 2001, 11, 443
14. Scammells, Peter; Gathergood, Nickolas; Ripper, Justin. Method for demethylation of N-methylmorphinans.

PCT Int. Appl. (2002), 25 pp. CODEN: PIXXD2 WO 2002016367 A1 20020228 CAN 136:200331 AN 2002: 157778 CAPLUS 15. McCamley, Kristy; Ripper, Justin A.; Singer, Robert D.; Scammells, Peter J. Efficient N-Demethylation of Opiate Alkaloids Using a Modified Nonclassical Polonovski Reaction. Journal of Organic Chemistry (2003), 68(25), 9847-9850. CODEN: JOCEAH ISSN: 0022-3263. CAN 140:77288 AN 2003:887142 CAPLUS 16. Chaudhuri, N. K., Servando, O., Markus, B., Galynkar, I., Sung, M-S., J. Indian Chem. Soc., 62, (1985) 899-903.

What is claimed is:

1. A one pot method for the N-demethylation and N-acylation of a tertiary N-methylated heterocycle comprising reacting a N-methylated heterocycle substrate with an acylating agent reactant other than haloformate esters in the presence of a metal catalyst to obtain a hydrocodone derivative product, wherein said substrate is hydrocodone.

2. A method according to claim 1 wherein the acylating agent has the general structure:

$$R_1-Y(R)(R_2)-C(=O)-Z-C(=O)-X(R')(R'_2)-R'_1$$

wherein:

X is C, CH, $CH_2$, $CF_2$, N, NR, O, S, SO, or $SO_2$,

Y is C, CH, $CH_2$, $CF_2$, N, NR, O, S, SO, or $SO_2$, each of R, $R_1$, $R_2$, R', $R'_1$, $R'_2$, independently, is H, SR, OR, $SiRR_1R_2$, $NR_1R_2$, Br, Cl, F, $CF_3$, $C_1$-$C_{19}$, CHO, COR, COOR, aryl, or heterocycle, and Z is O, N, or S.

3. A method according to claim 1 wherein the acylating agent has the general structure:

$$R_1-C(R)(R_2)-C(=O)-O-C(=O)-C(R')(R'_2)-R'_1$$

wherein R, $R_1$, $R_2$, R', $R'_1$, $R'_2$ are independently selected from H, SR OR $SiRR_1R_2$, $NR_1R_2$, Br, Cl, F, $CF_3$, $C_1$-$C_{19}$ alkyl and CHO.

4. The method according to claim 3, wherein the acylating agent is an anhydride selected from the group consisting of acetic anhydride, iso-butyric anhydride, n-propanoic anhydride, decanoic anhydride, dodecanoic anhydride, cyclopropylcarbonyl anhydride, cyclobutylcarbonyl anhydride, anhydrides derived from C1-C19 carboxylic acids and mixed anhydrides derived therefrom.

5. The method according to claim 4, wherein the anhydride is acetic anhydride.

6. A method according to claim 2 wherein the reactant is a dicarbonate in which Y is CO, Z is O and X is CO and has the general structure:

$$R_1-C(R)(R_2)-O-C(=O)-O-C(=O)-O-C(R')(R'_2)-R'_1$$

7. A method according to claim 6 wherein the dicarbonate is a mixed carbonate derivative of C1-C19 alcohols.

8. The method according to claim 6, wherein the dicarbonate is selected from the group consisting of dimethyl dicarbonate, di-tent-amyl dicarbonate, di-tert-butyl dicarbonate, diallyl pyrocarbonate, dibenzyl dicarbonate, diethyl pyrocarbonate, dimethyl dicarbonate, erythritol bis(carbonate) and mixed carbonates.

9. The method according to claim 8, wherein the dicarbonate is dimethyldicarbonate.

10. The method according to claim 8 wherein the dicarbonate is di-tert-butyl dicarbonate.

11. A method according to claim 2 wherein the acylating agent is a dicarbamic anhydride in which Y is N, Z is O and X is N and the acylating agent has the general structure:

$$R(R_1)N-C(=O)-O-C(=O)-N(R_1')R'$$

12. The method according to claim 11 wherein the dicarbamic anhydride is selected from the group consisting of N,N'-dimethylcarbamic anhydride, N,N'diethylcarbamic anhydride, diphenylcarbamic acid anhydride, N,N'diphenylcarbonic acid anhydride, N,N'diphenyldicarbonic diamide, N,N'(oxydicarbonyl)bisglycine dimethylester, pyrrole-1-carboxylic anhydride and mixtures thereof.

13. A method according to claim 12 wherein the dicarbamic anhydride is N,N'-dimethyl carbamic anhydride.

14. A method according to claim 12 wherein the dicarbamic anhydride is N,N'-diethyl carbamic anhydride.

15. A method according to claim 12 wherein the dicarbamic anhydride is diphenyl carbamic acid anhydride.

16. A method according to claim 12 wherein the dicarbamic anhydride is selected from the group consisting of N,N'-diphenyldicarbonic diamide.

17. A method according to claim 12 wherein the dicarbamic anhydride is N,N'(oxydicarbonyl)bisglycine dimethylester.

18. A method according to claim 12, wherein the dicarbamic anhydride is pyrrole-1-carboxylic anhydride.

19. The method according to claim 1, wherein the metal catalyst is selected from the group consisting of Pd, Pd(OAc)$_2$, PdCl$_2$, PdCl$_2$(PPh$_3$)$_4$, PdBr$_2$, Pd(acac)$_2$, Pd$_2$(dba)$_3$, Pd(dba)$_2$, Pd(PPh$_3$)$_4$, Cu, Fe, Ru, Co, Rh, Ir, Ni, Pt, Ge, Sn, Os, Cu, Ag, Au, and Pb.

20. The method according to claim 19, wherein the catalyst is selected from the group consisting of Cu, Fe, Ru, Co, Rh, Ir, Ni, Pd, Pt, Ge, and Sn.

21. The method according to claim 19, wherein the catalyst is selected from the group consisting of Os, Cu, Ag, Au, and Pb.

22. The method according to claim 21, wherein the catalyst is a palladium catalyst selected from the group consisting of Pd, Pd(OAc)$_2$, PdCl$_2$, PdCl$_2$(PPh$_3$)$_4$, PdBr$_2$, Pd(acac)$_2$, Pd$_2$(dba)$_3$, Pd(dba)$_2$, and Pd(PPh$_3$)$_4$.

23. The method according to claim 22, wherein the palladium catalyst is Pd(OAc)$_2$.

24. The method according to claim 1, wherein the catalyst is present in the range of from about 0.01 equivalents to 1.2 equivalents.

25. The method according to claim 24, wherein the catalyst is present in the range of from about 0.01 equivalents to 0.5 equivalents.

26. The method according to claim 24, wherein the catalyst is present in about 0.2 equivalents.

27. The method according to claim 1, wherein the reaction takes place in the presence of at least one solvent.

28. The method according to claim 27 wherein the solvent is selected from the group consisting of water, benzene, dioxane, toluene, lower (C1-C4) alcohols and mixtures thereof.

29. The method according to claim 28, wherein the at least one solvent is dioxane.

30. A method according to claim 1 wherein the product has a structure selected from the group consisting of:

wherein E is CH$_3$; G is O; J is H; X is C, CH, CH$_2$, CF$_2$, N, NR, O, S, SO or SO$_2$; each of R, R$_1$, and R$_2$ is H, SR, OR, SiRR$_1$R$_2$, NR$_1$R$_2$, Br, Cl, F, CF3, C1-C$_{19}$ alkyl, CHO, COR, COOR, aryl, or heterocycle.

31. A norhydrocodone derivative comprising a structure selected from the group below:

R = CH$_3$ (7)
R = CH(CH$_3$)$_2$ (10)
R = CH$_2$CH$_3$ (11)
R = (CH$_2$)$_8$CH$_3$ (12)
R = (CH$_2$)$_{10}$CH$_3$ (13)

32. A derivative according to claim 31 wherein R is CH$_3$.

33. A derivative according to claim 31 wherein R is CH(CH$_3$)$_2$.

34. A derivative according to claim 31 wherein R is CH$_2$CH$_3$.

35. A derivative according to claim 31 wherein R is (CH$_2$)$_8$CH$_3$.

36. A derivative according to claim 31 wherein R is (CH$_2$)$_{10}$ CH$_3$.

37. A one pot method for the N-demethylation and N-acylation of a tertiary N-methylated heterocycle comprising reacting a N-methylated heterocycle substrate with an acylating agent reactant selected from the group consisting of anhydrides and dicarbonates in the presence of a metal catalyst to obtain a hydrocodone derivative product, wherein said substrate is.

38. A one pot method for the N-demethylation and N-acylation of a tertiary N-methylated heterocycle comprising reacting hydrocodone with an acylating agent reactant selected from the group consisting of anhydrides and dicarbonates in the presence of a metal catalyst to obtain a hydrocodone derivative product.

* * * * *

UNITED STATES PATENT AND TRADEMARK OFFICE
CERTIFICATE OF CORRECTION

| | | |
|---|---|---|
| PATENT NO. | : 7,999,104 B2 | Page 1 of 1 |
| APPLICATION NO. | : 11/771191 | |
| DATED | : August 16, 2011 | |
| INVENTOR(S) | : Robert James Carroll et al. | |

It is certified that error appears in the above-identified patent and that said Letters Patent is hereby corrected as shown below:

Column 16, line 15, "di-tent" should read --di-tert--.
Column 16, line 40, "N,N'diethylcarbamic" should read --N,N' -diethylcarbamic--.
Column 16, line 42, "N,N'diphenylcarbonic" should read --N,N' -diphenylcarbonic--.
Column 16, line 43, "N,N'diphenyldicarbonic" and "N,N'(oxydicarbonyl)" should read
--N,N'-diphenyldicarbonic-- and --N,N'-(oxydicarbonyl)--.
Column 16, line 66, "1r" should read --Ir--.
Column 17, line 2, "1r" should read --Ir--.
Column 17, line 51, "CF3" should read --CF--.
Column 18, line 45, "strate is." should read --strate is hydrocodone--.

Signed and Sealed this
Third Day of July, 2012

David J. Kappos
*Director of the United States Patent and Trademark Office*